US012465513B2

(12) United States Patent
Altaher

(10) Patent No.: US 12,465,513 B2
(45) Date of Patent: Nov. 11, 2025

(54) BREATHING ASSIST ASSEMBLY AND METHOD

(71) Applicant: Breathe Up LLC, Maple Grove, MN (US)

(72) Inventor: Amjad Hesham Altaher, Maple Grove, MN (US)

(73) Assignee: Breathe Up LLC, Maple Grove, MN (US)

( * ) Notice: Subject to any disclaimer, the term of this patent is extended or adjusted under 35 U.S.C. 154(b) by 217 days.

(21) Appl. No.: 18/102,006

(22) Filed: Jan. 26, 2023

(65) Prior Publication Data

US 2023/0398014 A1 Dec. 14, 2023

Related U.S. Application Data

(60) Provisional application No. 63/351,665, filed on Jun. 13, 2022.

(51) Int. Cl.
*A61F 5/08* (2006.01)

(52) U.S. Cl.
CPC .................................... *A61F 5/08* (2013.01)

(58) Field of Classification Search
CPC .................................................. A61F 5/08
See application file for complete search history.

(56) References Cited

U.S. PATENT DOCUMENTS 5,533,499 A * 7/1996 Johnson .................... A61F 5/08 606/204.45
5,669,377 A 9/1997 Fenn
5,685,292 A * 11/1997 Fenn ........................ A62B 9/06 128/207.18
5,817,039 A 10/1998 Raunig
5,890,486 A 4/1999 Mitra
5,976,173 A * 11/1999 Berke ....................... A61F 5/08 606/204.45
6,390,089 B1 5/2002 Lacouture
6,419,687 B1 * 7/2002 Berke ....................... A61F 5/08 606/204.45
2003/0187374 A1 10/2003 Nishioka
2009/0205640 A1 8/2009 Kehiaian

* cited by examiner

*Primary Examiner* — Julian W Woo
(74) *Attorney, Agent, or Firm* — Bradley J. Thorson; DeWitt LLP

(57) ABSTRACT

Breathing is assisted through the use of an assembly including a panel having three end sections serving as attachment points, two of which are adapted to be attached to an ala of a user's nose and one of which is adapted to be attached to the user's forehead, the panel incorporating reinforcing members adapted to provide pulling force between each of the three attachments point to open the nasal passages.

18 Claims, 7 Drawing Sheets

BREATHING ASSIST ASSEMBLY AND METHOD

CROSS-REFERENCE TO RELATED APPLICATIONS

This application is a non-provisional application of Application No. 63/351,665, filed Jun. 13, 2022, and claims priority from that application which is also deemed incorporated by reference in its entirety in this application.

STATEMENT REGARDING FEDERALLY SPONSORED RESEARCH OR DEVELOPMENT

Not Applicable

BACKGROUND OF THE INVENTION

(1) Field of the Invention

The invention relates to breathing assist devices and more particularly pertains to improved new breathing assist devices for expanding the nasal passages of a user to assist a user in breathing through the nose.

(2) Discussion of the Prior Art

Various breathing assist devices are known in the prior art. For example, U.S. Pat. No. 5,669,377, granted to Arther C. Fenn on Sep. 23, 1997, discloses a nasal band used to improve breathing. The band is designed to lift-up the tip of the nose, enlarge the nostrils and shorten the effective length of the nasal passageways. The band has a lower end comprising a base for detachably engaging the tip of the nose and upper end positioned in registration with and operatively connected to the base for detachably engaging a portion of a patient's face above the tip of the nose. The upper end cooperates with the base for lifting the tip of the nose to enlarge the patient's nostrils and decrease nasal resistance to enhance breathing. An intermediate adhesive layer and a lower bottom peelable layer are provided. The adhesive runs along the entire length of the band as does the peelable layer. This design allows the middle part to adhere to the bridge of the nose. This arrangement does not supply any force to pull on either ala of the nose to open the passageways. Likewise, adherence of the adhesive layer to the entire length of the nose is less than ideal.

U.S. Patent Publication No. 2009/0205640 of Gaitag Kehiaian describes devices adhesively affixed to the nasal walls outside of the nose to gently pull the nasal walls outwardly thereby enhancing the passage of air through the nose. This publication further explains that such devices do not provide adequate retaining forces. In particular, the outward forces exerted on the nasal cartilages by such devices do not hold the nasal passages sufficiently open. The publication proposes a possible solution involving the use of a nose strip comprising a first end, a second end, and an adhesive layer disposed on at least a portion of the first end, and a portion of the second end. The first end is configured to adhere to a first skin tissue located above a bridge of a user's nose and a distance away from a tip of the user's nose. The second end is configured to adhere to a second skin tissue located above the first skin tissue, wherein the first skin tissue is pulled in a direction generally towards the user's eyes. While devices such as those disclosed in the Kehiaian publication offer some benefit, they do not satisfactorily resolve breathing issues for all users.

BRIEF SUMMARY OF THE INVENTION

The present invention overcomes the deficiencies of prior art by providing a breathing assist device comprising a horizontal portion and a vertical portion extending from the horizontal portion. The horizontal portion has a first end section and a second end section and a first intermediate section, a first adhesive pad coupled to the first end section, and a second adhesive pad coupled to the second end section. The first intermediate section comprises a first reinforcing member biased toward a first predetermined configuration.

More specifically, the horizontal portion is adapted to extend from a first ala of a person's nose to a second ala of said person's nose. When so positioned, the first adhesive pad is adapted for releasable engagement to temporarily fasten the first end section to the first ala, and the second adhesive pad is adapted for releasable engagement to temporarily fasten the second end section to the second ala. Significantly, the horizontal portion is adapted to provide a first pulling force to both the first ala and the second ala. This first pulling force is provided at least in part by the first reinforcing member being biased toward a first predetermined configuration.

The vertical portion has a second intermediate section, a third end section and a third adhesive pad coupled to the third end section. The second intermediate section comprises a second reinforcing member biased toward a second predetermined configuration. More specifically, the vertical portion is adapted to extend to the user's forehead from the horizontal portion when the first end section is fastened to the first ala and the second end section is fastened to the second ala. The third adhesive pad is adapted for releasable engagement to temporarily fasten the third end section to the user's forehead. When the third adhesive pad is so attached, the vertical portion provides a second pulling force to both the first ala and the second ala. This second pulling force is provided at least in part by the second reinforcing member being biased toward the second predetermined configuration.

Selected embodiments of the present invention may include additional features. For example, the first reinforcing member and the second reinforcing member may be separate structures in some embodiments. In other embodiments, the first reinforcing member and the second reinforcing member may be formed together as a single structure. In some embodiments, the adhesive pads may simply be a layer of adhesive applied directly to the surfaces of the three end sections of the device. In other embodiments, each adhesive pad may comprise a separate substrate bonded to an end section of the device and coated with a layer of adhesive adapted to temporarily fasten an end section of the device to a user's skin. In some embodiments, each pad may be provided with a separate removable coverings to prevent the adhesive from sticking to another surface or drying out prior to use. In other embodiments, a single removable covering adapted to cover all three pads simultaneously may be used. In some embodiments, the device may be constructed as a single layer plus the adhesive applied to the three end sections. Other embodiments include multiple layers.

Additionally, the materials used to construct the device, and particularly the first and second reinforcing members, may vary. For example, the first or second reinforcing member may be constructed of a suitable plastic, metal, or other resiliently bendable spring-like material. Use of such a spring-like material will serve to bias the reinforcing member toward a predetermined configuration chosen to provide a desired pulling force.

The first or second reinforcing member may also be constructed of a stretchable elastic material. In such cases, the first reinforcing member has a first predetermined configuration, i.e., its relaxed state. The use of the stretchable elastic material allows the horizontal portion to be stretched across the apex of the nose for attachment of the first end portion to the first ala and attachment of the second end portion to the second ala. When so stretched and attached, the stretchable elastic material of the first reinforcing member provides a pulling force as the material seeks to return to its predetermined configuration, i.e., its relaxed state. Likewise, the second reinforcing member may be made of a resilient material. In such cases, the second reinforcing member has a second predetermined configuration, i.e., its relaxed state. The use of the stretchable elastic material allows the vertical portion to be stretched from the horizontal portion past the bridge of the user's nose for attachment of the third end portion to user's forehead. When so stretched and attached, the stretchable elastic material of the second reinforcing member provides a second pulling force as the stretchable elastic material seeks to return to its predetermined configuration, i.e., its relaxed state.

In still other embodiments, the reinforcing members may be made of a shape memory alloy such as nitinol or a shape memory polymer such as thermoplastic polyurethane. Such materials have the ability to recover their original shape from a significant and seemingly plastic deformation when a particular stimulus is applied. Such a stimulus could be, for example, exposure to body heat, light, moisture, or a change in pH. When used to construct a reinforcing member of the present invention, the device is formed with the reinforcing member in a predetermined configuration, i.e., its original shape. The reinforcing members can then be deformed, permitting the desired attachment of the end sections of the device to the first ala, the second ala, and forehead of the user. A suitable stimulus can then be applied causing the shape memory material of the reinforcing member(s) to try to return to the original shape and thereby provide a pulling force.

In all embodiments, the reinforcing members and adhesive pads must be adapted so the reinforcing members provide sufficient force to cause the nostrils to expand sufficiently to enhance breathing without causing the adhesive pads to inadvertently detach from the user.

BRIEF DESCRIPTION OF THE DRAWINGS

The foregoing features, objects and advantages of the invention will become apparent to those skilled in the art from the following detailed description and with reference to the following drawings in which like numerals in the several views refer to corresponding parts.

DETAILED DESCRIPTION

Figure 1:
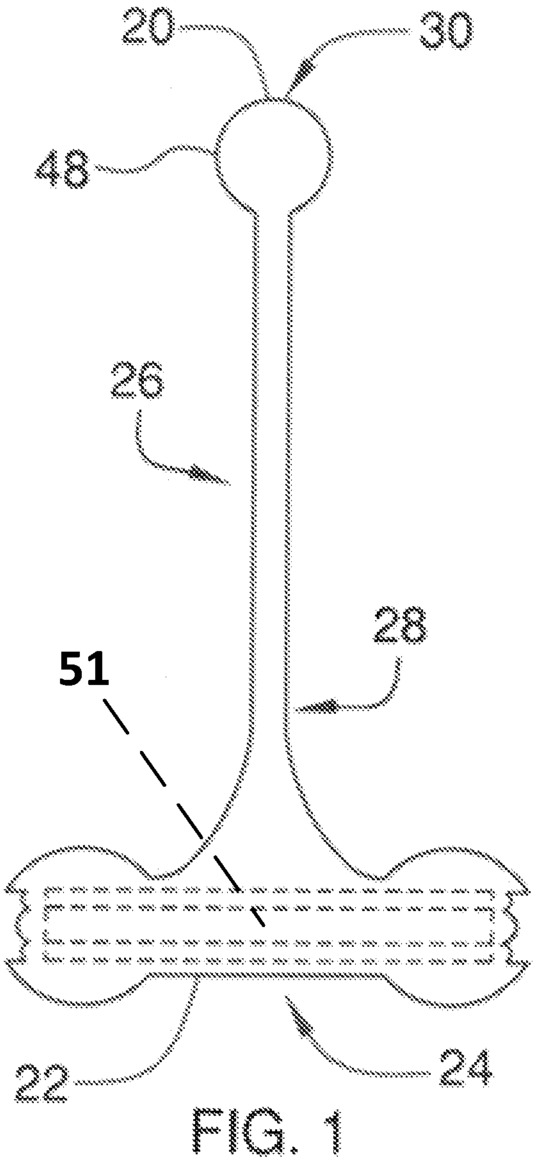
FIG. 1 is a front view of a breathing assist assembly made in accordance with the present inventions.

This description of the preferred embodiment is intended to be read in connection with the accompanying drawings, which are to be considered part of the entire written description of this invention. In the description, relative terms such as "lower", "upper", "horizontal", "vertical", "above", "below", "up", "down", "top" and "bottom", "under", as well as derivatives thereof (e.g., "horizontally", "downwardly", "upwardly", "underside", etc.) should be construed to refer to the orientation as then described or as shown in the drawings under discussion. These relative terms are for convenience of description and do not require that the apparatus be constructed or operated in a particular orientation. Terms such as "connected", "connecting", "attached", "attaching", "joined", and "joining" are used interchangeably and refer to one structure or surface being secured to another structure or surface or integrally fabricated in one piece unless expressly described otherwise.

With reference now to the drawings, and in particular to FIGS. 1 through 9 thereof, a new breathing assist device embodying the principles and concepts of an embodiment of the disclosure and generally designated by the reference numeral 10 will be described.

As best illustrated in FIGS. 1 through 9, the breathing assist assembly 10 generally comprises a panel 12 having a front side 14, a rear side 16, and a perimeter edge 18. The panel 12 will typically be comprised of flexible materials including plastics, elastomers and the like. The perimeter edge 18 includes an upper edge 20 and a lower edge 22 when the panel 12 is orientated vertically as shown in FIG. 1. The panel 12 has a horizontal portion 24 includes the lower edge 22 and a vertical portion 26 extending upwardly from the horizontal portion 24 and including the upper edge 20. The vertical portion 26 has proximal end section 28 and a distal end section 30 with respect to the horizontal portion 24. The distal end section 30 includes the upper edge 20 and the proximal end section 28 is spaced from a first lateral edge 32 and a second lateral edge 34 of the horizontal portion 24. Thus, the panel 12 has a generally inverted "T" shape.

The horizontal portion 24 has a width measurement from the first lateral edge 32 to the second lateral edge 34 that will typically be from 1.0 inches to 3.0 inches. The vertical portion 26 has a width measurement that will usually be less than 0.5 inches, and more typically be less than 0.4 inches. The vertical portion 26 has a height measurement from the proximal end 28 to the distal end 30 that is from 2.0 inches to 5.0 inches, and the horizontal portion 24 has a height measurement that is greater than the width measurement of the vertical portion 26. Subsequently, the vertical portion 26 will be relatively narrow to prevent inhibiting a person's vision while utilizing the assembly 10, as is apparent from FIG. 6.

Figure 2:
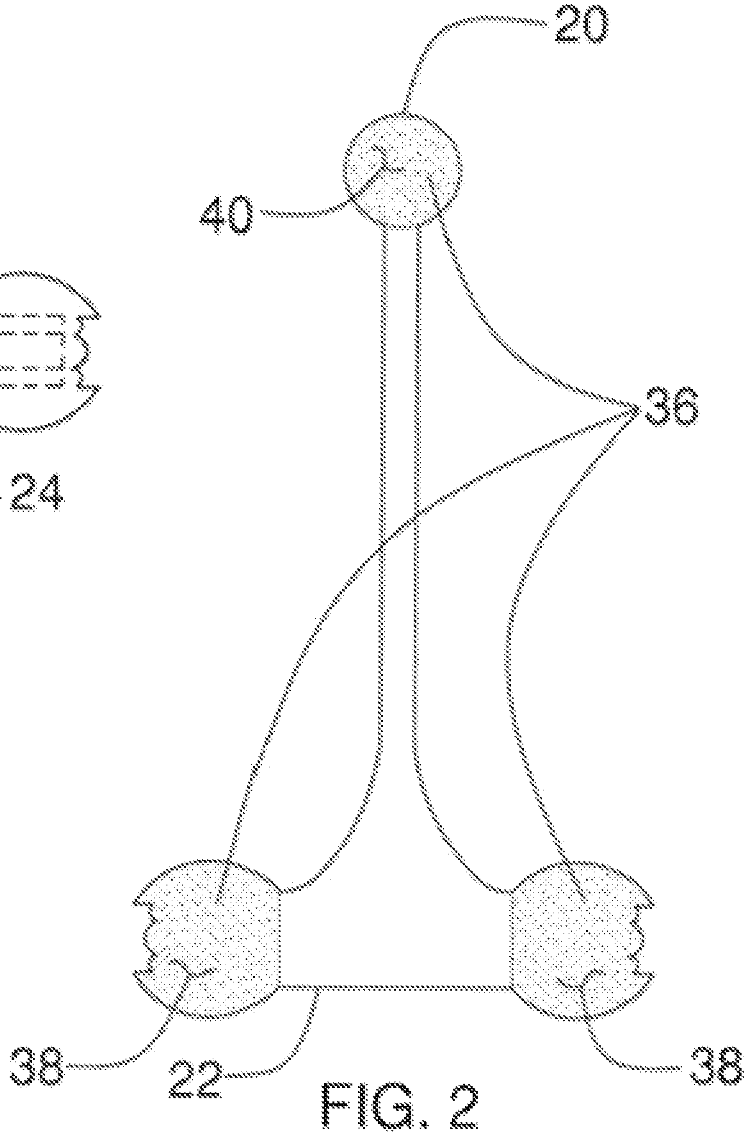
FIG. 2 is a rear view of the breathing assist assembly of FIG. 1.
Figure 3:
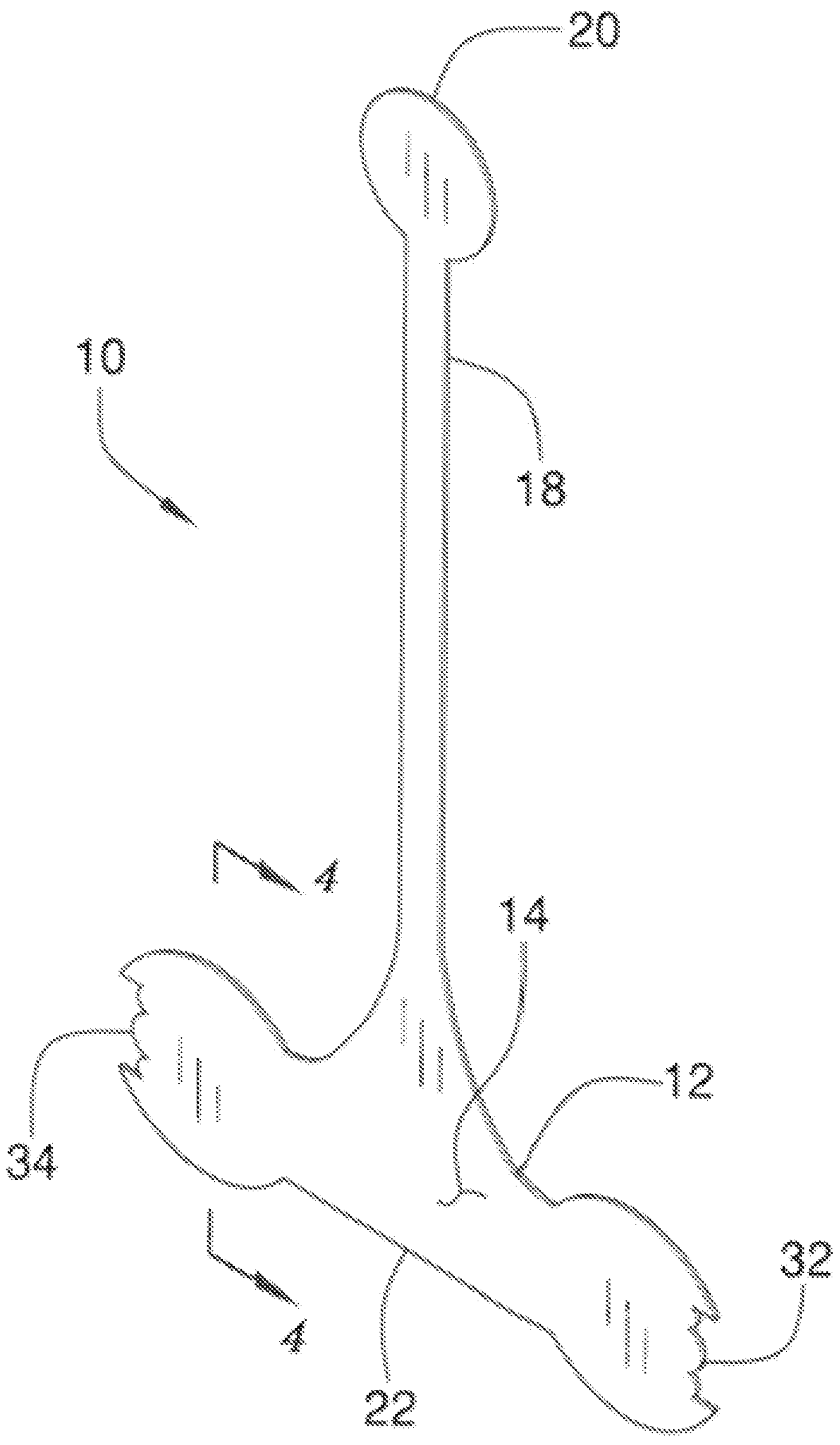
FIG. 3 is a front isometric view of the breathing assist assembly of FIG. 1.
Figure 5:
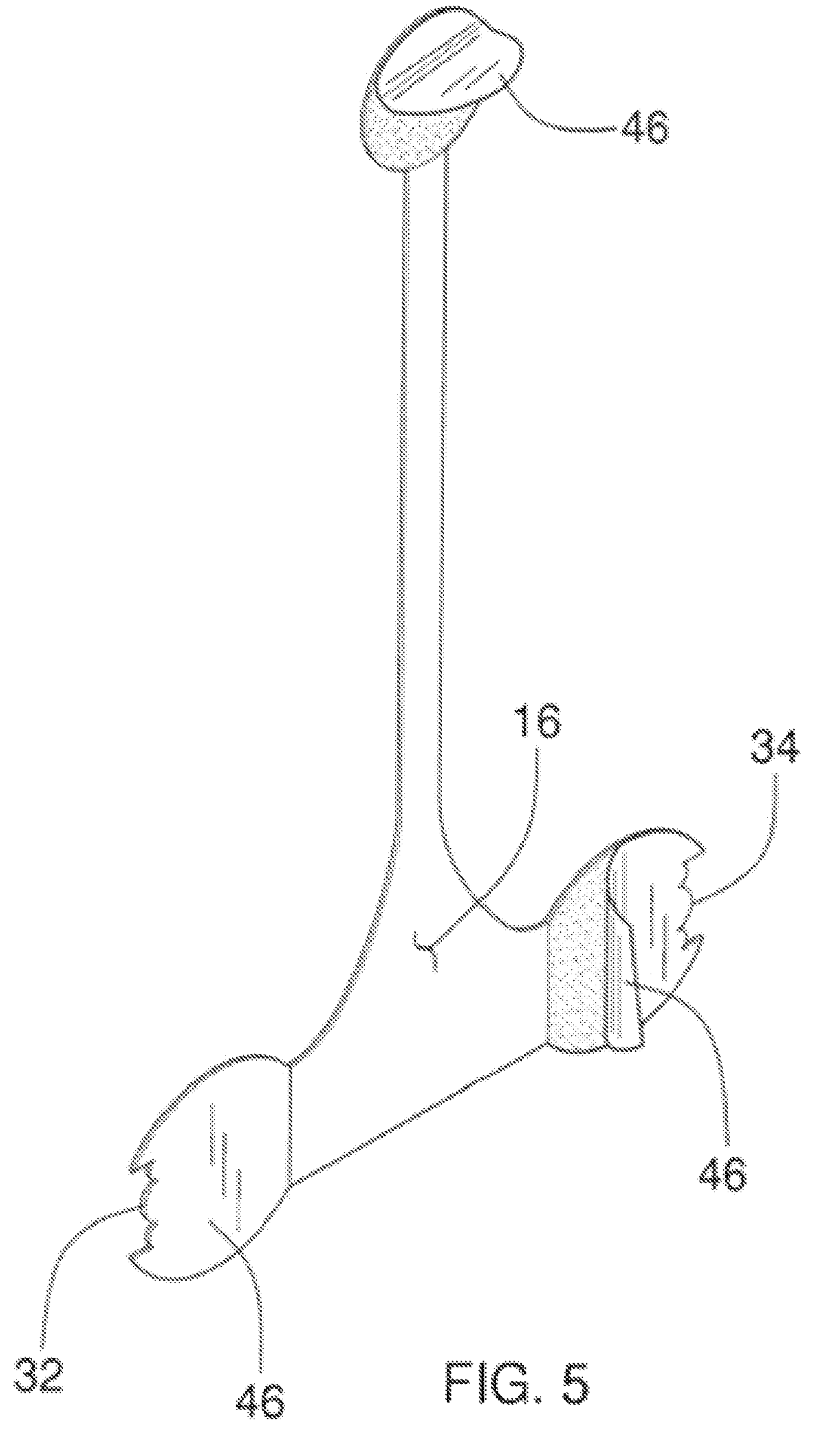
FIG. 5 is a rear isometric view of the breathing assist assembly of FIG. 1.
Figure 8:
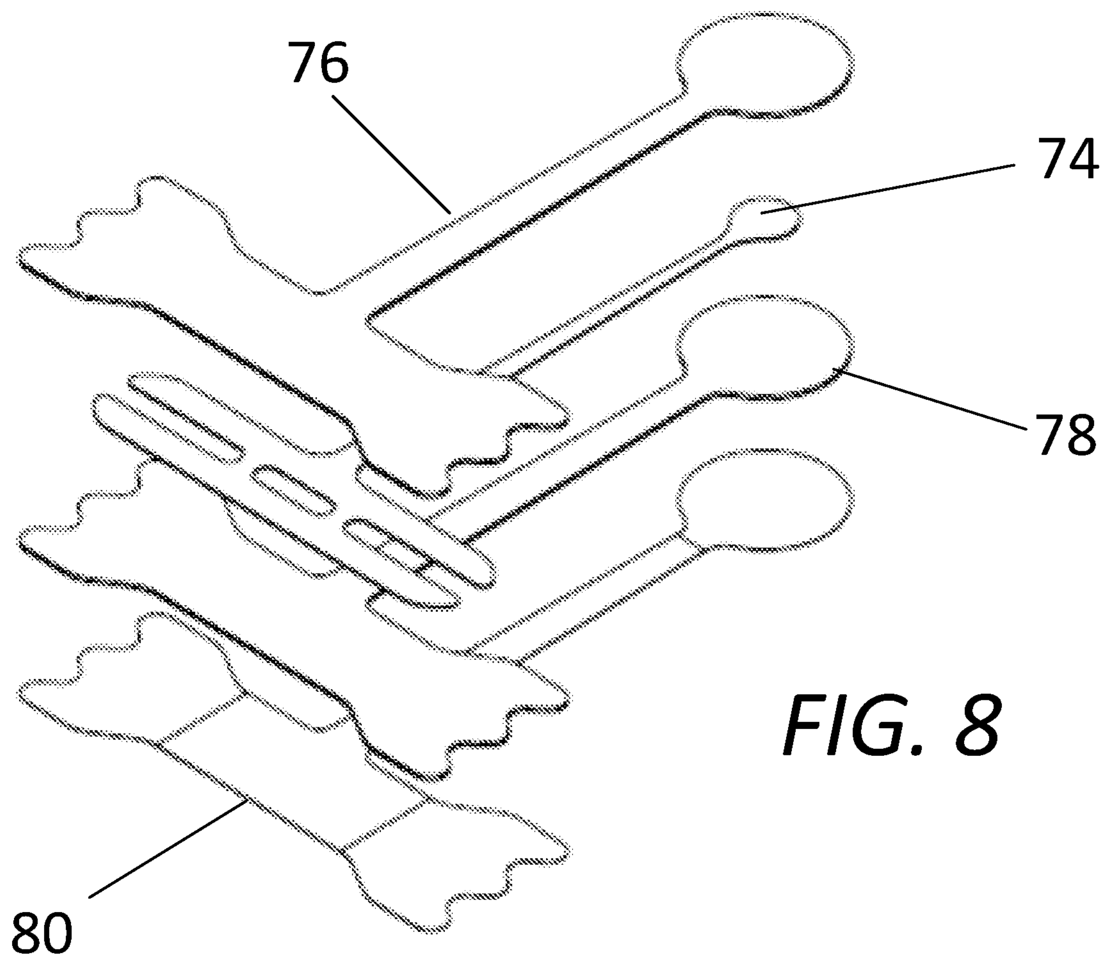
FIG. 8 is an exploded isometric view of an alternative breathing assist assembly made in accordance with the present invention.

The rear side 16 has a plurality of adhesive pads 36 thereon configured for releasable engagement with a person's skin. The adhesive pads or sections 36 include at least one nose pad 38 positioned on the rear side 16 of the horizontal portion 24. However, as shown in FIG. 2, the adhesive pads 38 of the horizontal portion comprise two areas of the adhesive each positioned adjacent to one of the first 32 and second 34 lateral edges and defining first and second end sections. The adhesive pads 36 further include at least one forehead pad 40 positioned on the rear side 16 of the vertical portion 26 adjacent to the upper edge 20 defining a third end section. A majority of the surface area of the rear side 16 of the vertical portion 26 is free of the adhesive such that an area of the vertical portion 26 positioned over a nasal bridge 44 of a person's nose 42 is free of the adhesive. Removably coverings 46 are removably positioned on the adhesive pads as shown in FIG. 5. Alternatively, a single covering or layer 80 may cover all three pads 36 as shown in FIG. 8. As used herein, each of the adhesive pads 36 may comprise an adhesive adapted to temporarily bond the device to the user's skin applied to a portion of the panel or may be a separate substrate having a first side permanently bonded to the panel and a second side coated with an adhesive adapted to temporarily bond the device to the user's skin.

In one embodiment, as shown in FIG. 5, a widened sector 48 of the vertical portion 26 may be provided wherein the widened sector 48 includes the upper edge 20. In some embodiments the widened section 48 extends less than 25% of a distance from the upper edge 20 to the horizontal portion 24. The vertical portion 26 has the adhesive positioned only on the widened sector 48 and therefore at least 75% of the distance of the rear side 16 of the vertical portion 26, extending upwardly from the horizontal portion 24, does not include any adhesive. This prevents a majority of a height of the vertical portion 26 from adhering to a person's face. The widened sector 48 provides a larger surface area to ensure sufficient adhesion to the person's skin and though shown in a circular shape may be provided in different shapes as well.

In some embodiments, the horizontal portion 24 may be resistant to bending along a line extending from the first lateral edge 32 to the second lateral edge 34. This is common for breathing aids which are utilized for opening the nostrils 52 and nasal cavity of a person. This resilience may be achieved by the material of which the horizontal portion 24 is constructed. Preferably, this is achieved by constructing the horizontal portion 24 so that it includes an internal first reinforcing member such as 51 in FIG. 1 or 70 in FIGS. 8 and 9. The first reinforcing member 51/70 may be made of plastic, metal, or other resiliently bendable spring-like material having a predetermined configuration, i.e., its relaxed state. The first reinforcing member 51/70 is deformed as the end sections of the horizontal portion are attached to the first ala 90 and second ala 92 of a user's nose 42. The first reinforcing member 51/70 is biased toward its predetermined configurations and thus further adapted to provide a pulling force as the material seeks to return to its relaxed state.

The first reinforcing member 51/70 may alternatively be constructed of a stretchable elastic material having a first predetermined configuration, i.e., its relaxed state. A first reinforcing member 51/70 constructed of a stretchable elastic material is adapted to be stretched across the apex 91 of the user's nose 42 between the two ala 90 and 92 for attachment of each end section of the horizontal portion to an ala of a user's nose 42. The reinforcing member is biased toward its relaxed state and when so attached provides a pulling force as the material seeks to return to its relaxed, unstretched state.

In still other embodiments, the reinforcing member 51/70 may be made of a shape memory alloy such as nitinol or a shape memory polymer such as thermoplastic polyurethane. Such materials recover their original shape from a significant and seemingly plastic deformation when a particular stimulus is applied. Such a stimulus could be, for example, exposure to body heat, light, moisture, or a change in pH. When used to construct reinforcing member 51/70, the reinforcing member is formed in a predetermined configuration, i.e., its original shape. The reinforcing member 51/70 can then be deformed, permitting the desired attachment of the first end section to the first ala and the second end section to the second ala. Such materials are biased toward their redetermined configuration in the sense that when a suitable stimulus is applied the shape memory material of the reinforcing member 51/70 will try to return to the original shape and thereby provide a pulling force on both the first ala 90 and the second ala 92.

Figure 4:
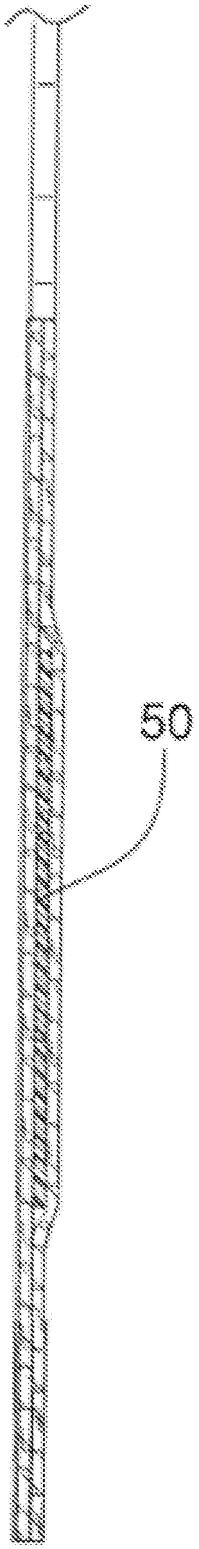
FIG. 4 is a cross-sectional view of the breathing assist assembly of FIG. 1 taken along line 4-4 of FIG. 3.
Figure 9:
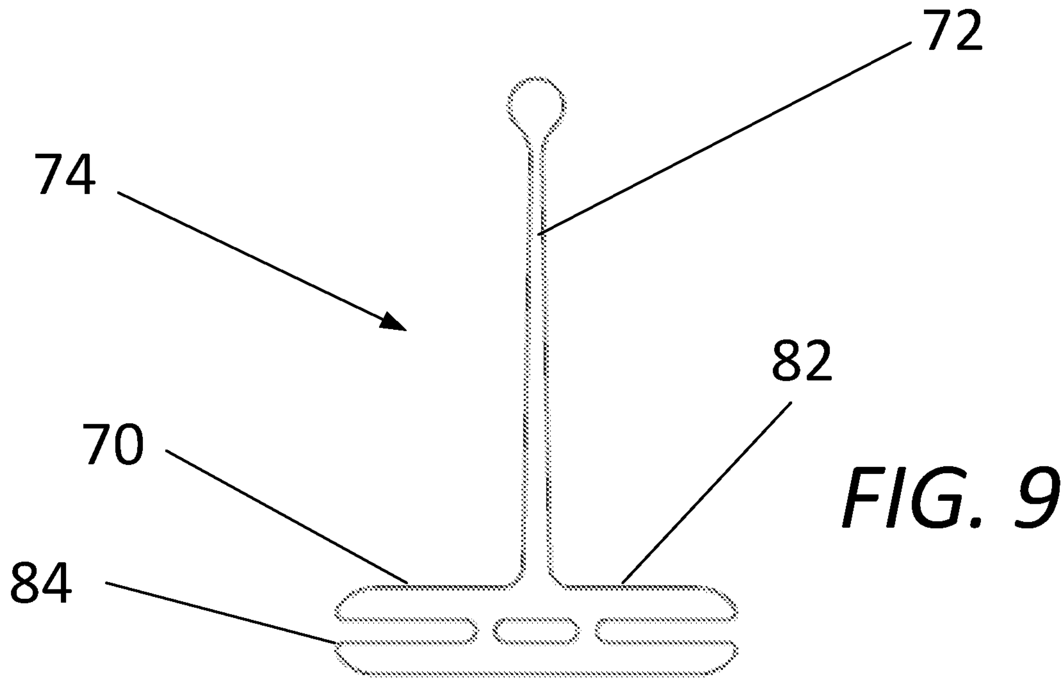
FIG. 9 is a front view if one of the layers of the alternative breathing assist assembly of FIG. 8.

The vertical portion 26 will typically be flexible and less resistant to bending than the horizontal portion 24. Moreover, the vertical portion 26 is resilient. This resilience may be achieved by the material of which the horizontal portion 24 is constructed. This resilience may be achieved by providing an internal reinforcing member 50 as shown in FIG. 4 or a second reinforcing member 72 as shown in FIGS. 8 and 9. Like the first reinforcing member 51/70, the reinforcing member 50 or second reinforcing member 72 may be constructed of a suitable plastic, metal, or other resiliently bendable spring-like material. Use of such a spring-like material will serve to bias the reinforcing member 50/72 toward a predetermined configuration chosen to provide a desired pulling force. The second reinforcing member may also be constructed of a stretchable elastic material. For example, the second reinforcing member may be made of a resilient material capable of being stretched from its predetermined configuration, i.e., relaxed state, to permit attachment of the third end section to the user's forehead 54 while the first end section is attached to the first ala 90 and the second end section is attached to the second ala 92. The second reinforcing member is biased toward its relaxed state. As such, when so attached, the second reinforcing member 50/72 provides a second pulling force as the material of the second reinforcing member 50/72 seeks to return to its relaxed state. In still other embodiments, the reinforcing member 50/72 may be made of a shape memory material such as those previously identified. When a shape memory material is used to construct reinforcing member 50/72, the reinforcing member 50/72 is formed in a predetermined configuration, i.e., its original shape. The reinforcing member 50/72 can then be deformed, permitting the desired attachment of the first end section to the first ala and the second end section to the second ala and the third end section to the forehead 54. A suitable stimulus can then be applied causing the shape memory material of the reinforcing member 50/72 to try to return to the original shape and thereby provide a second pulling force from the forehead to both the first ala 90 and the second ala 92

In all embodiments, the reinforcing members 51/70 and 50/72 and adhesive pads 38 and 40 must be adapted so the reinforcing members provide enough force to cause the nostrils to expand sufficiently to enhance breathing without causing the adhesive pads 38 and 40 to inadvertently detach from the user.

FIGS. 8 and 9 show an embodiment of the present invention in which the internal first reinforcing member 70 and the internal second reinforcing member 72 are made a single assembly 74. As shown, assembly 74 is sandwiched between two outer layers 76 and 78. These layers may be made of a resilient woven fabric or other flexible materials including plastics, elastomers and the like. FIG. 8 also shows a layer 80 that covers the adhesive applied to the three end sections. Layer 80 can be peeled away as a single piece to expose the adhesive pad 38 and 40 for application to the skin of the user. Note that in this embodiment, the edges of the three ends are serrated which aids in preventing the adhesive from detaching inadvertently during use as a result of normal movement of the skin. Also, the internal first reinforcing member 70 is divided into two elongate sections 82 and 84 separated by spaces so that the device does not unduly interfere with the motion of the nose 42 during breathing which could cause unnecessary irritation of the tissue of the nose 42 to which the horizontal portion 24 is attached.

Figure 6:
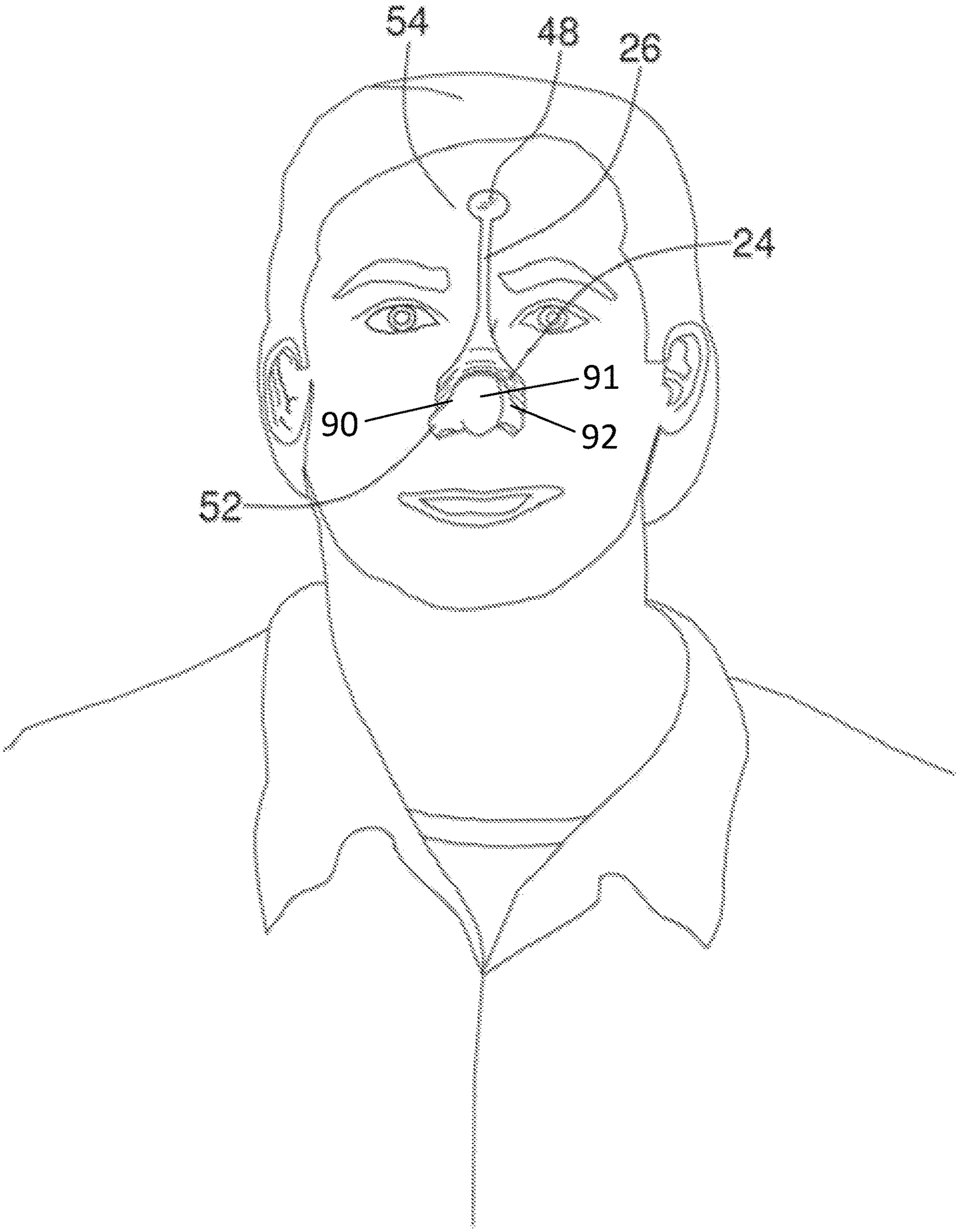
FIG. 6 is a front in-use view of the breathing assist assembly of FIG. 1.
Figure 7:
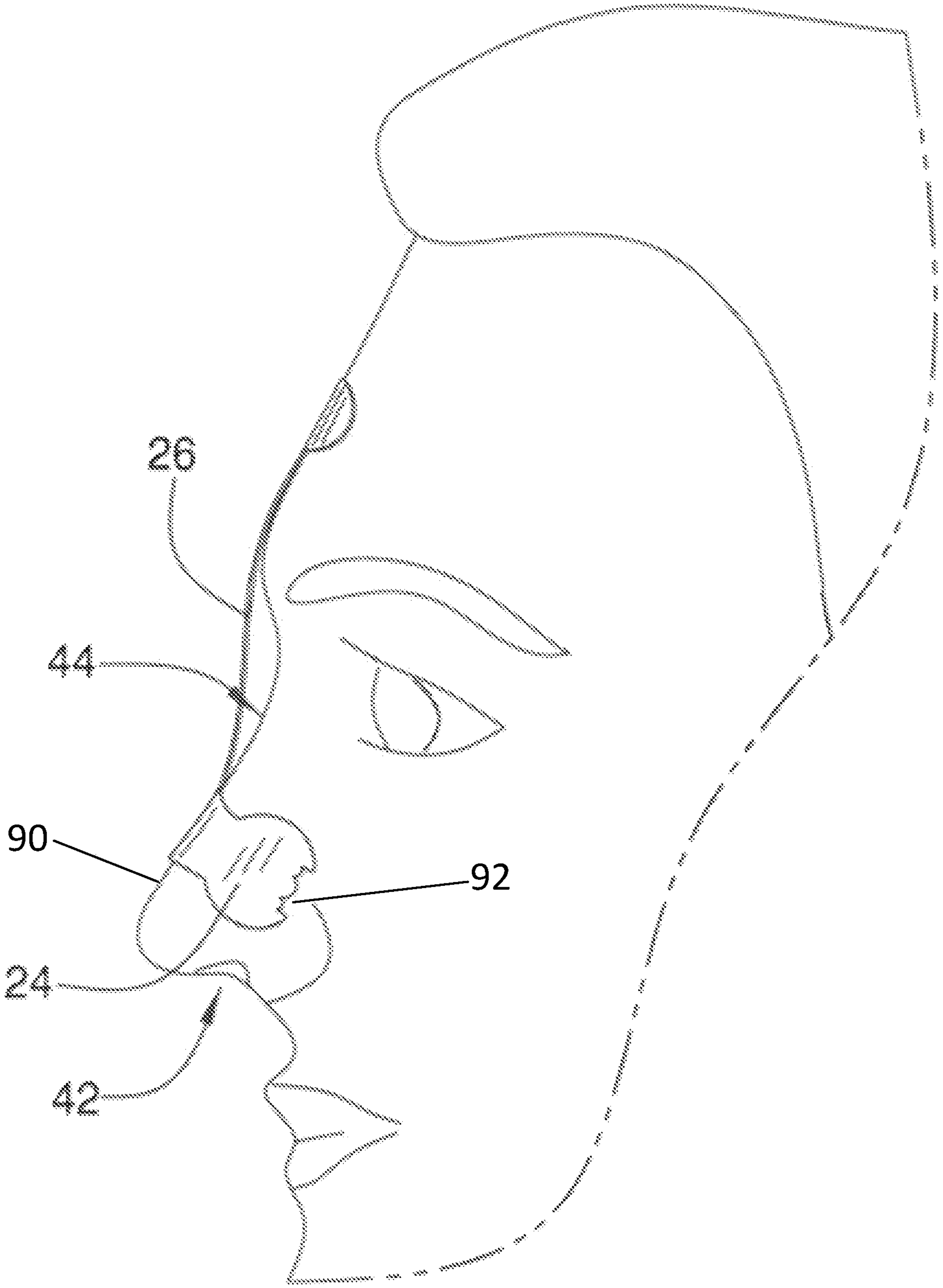
FIG. 7 is a side in-use view of the breathing assist assembly of FIG. 1.

In use, the horizontal portion 24 is positioned on a person's face as shown in FIG. 6. The first end section of the horizontal portion 24 is attached to the first ala 90 and the second end section of the horizontal portion 24 is attached to the second ala 92 with the horizontal portion 24 extension over the apex 91 of the person's nose 42. When so attached, the horizontal portion 24 applies a first force causing the nostrils 52 to widen, i.e. dilate. The rear side 16 of the vertical portion 26, adjacent to the upper edge 20, i.e., the third end portion, is attached to the person's forehead 54 so that the vertical portion 26 extends over and is spaced from the person's nose 42 as shown in FIG. 7. This will apply a second force pulling the nostril 52 area and tip of the nose 42 toward the forehead 54 to further open (dilate) the nasal passages.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded.

A reference to an element by the indefinite article "a" does not exclude the possibility that more than one of the element is present, unless the context clearly requires that there be only one of the elements.

I claim:

1. A breathing aid assembly comprising:

a horizontal portion having a first end section and a second end section and a first intermediate section, a first adhesive pad coupled to said first end section and a second adhesive pad coupled said second end section, wherein said first intermediate section comprises a first reinforcing member biased toward a first predetermined configuration, and wherein said horizontal portion is adapted to extend from a first ala of a person's nose to a second ala of said person's nose, said first adhesive pad is adapted for releasable engagement to temporarily fasten said first end section to said first ala, said second adhesive pad is adapted for releasable engagement to temporarily fasten said second end section to second ala, and said horizontal portion is adapted to provide a first pulling force to both the first ala and the second ala, said pulling force provided at least in part by the first reinforcing member being biased toward a first predetermined configuration; and a vertical portion extending from the horizontal portion and having a second intermediate section, a third end section and a third adhesive pad coupled to said third end section, wherein said second intermediate section comprises a second reinforcing member biased toward a second predetermined configuration, and wherein said vertical portion is adapted to extend to the person's forehead from said horizontal portion when the first end section is fastened to the first ala and the second end section is fastened to the second ala, and wherein said third adhesive pad is adapted for releasable engagement to temporarily fasten said third end section to the person's forehead and provide a second pulling force to both the first ala and the second ala, said second pulling force provided at least in part by the second reinforcing member being biased toward the second predetermined configuration.

2. The breathing aid assembly of claim 1 wherein said second intermediate section is free of adhesive.

3. The breathing aid assembly of claim 1 wherein said first intermediate section is made of a resilient material.

4. The breathing aid assembly of claim 1 wherein said horizontal portion is made of a resilient material.

5. The breathing aid assembly of claim 1 wherein said vertical portion is made of a resilient material.

6. The breathing aid assembly claim 1 wherein the intermediate section of said horizontal portion comprises a first plurality of layers.

7. The breathing aid assembly of claim 1 wherein said second intermediate section is made of a second plurality of layers.

8. The breathing aid assembly of claim 1 wherein said third end section is wider than said second intermediate section.

9. The breathing aid of claim 1 wherein said first end section and said second end section are wider than the first intermediate section.

10. The breathing aid assembly of claim 1 wherein said second intermediate section is adapted to be spaced from the person's skin when the first end section is temporarily fastened to the person's first ala, the second end section is fastened to the person's second ala, and the third end section is attached to the person's forehead.

11. The breathing aid assembly of claim 1 wherein the first end section and the second end section each have a serrated lateral edge.

12. The breathing aid assembly of claim 1 wherein said first reinforcing member is made of a material selected from a group consisting of a metal or a plastic.

13. The breathing aid assembly of claim 1 wherein said second reinforcing member is made of a material is selected from a group consisting of a metal or a plastic.

14. The breathing aid assembly of claim 1 wherein at least one of said first reinforcing member and said second reinforcing member is made of a shape memory material.

15. The breathing aid assembly of claim 1 wherein at least one of said first reinforcing member and said second reinforcing member is made of a resiliently bendable spring-like material having a relaxed state.

16. The breathing aid assembly of claim 1 wherein at least one of said first reinforcing member and said second reinforcing member is made of a resiliently stretchable material having a relaxed state.

17. The breathing aid assembly of claim 1 further comprising at least one releasable covering adapted to temporarily cover at least one of the first, second and third adhesive pads.

18. A method of assisting a person while breathing including the steps of:

(a) providing a breathing aid assembly comprising (i) a horizontal portion having a first end section and a second end section and a first intermediate section, a first adhesive pad coupled to said first end section and a second adhesive pad coupled said second end section, and (ii) a vertical portion extending from the horizontal portion and having a second intermediate section, a third end section and a third adhesive pad coupled to said third end section;

(b) positioning the horizontal portion across the person's nose, releasably engaging the first adhesive pad with a first ala of the person's nose to temporarily fasten said first end section to said first ala, and releasably engaging the second adhesive pad with a second ala of the person's nose to temporarily fasten said second end section to said second ala so that the horizontal portion provides a first pulling force to both the first ala and the second ala; and (c) extending the vertical portion from the horizontal portion over the person's nose, and releasably engaging the third adhesive pad with a portion of the person's forehead to temporarily fasten said third end section to the person's forehead and provide a second pulling force to both the first ala and the second ala.

* * * * *